United States Patent [19]

Maguire et al.

[11] 4,227,891

[45] Oct. 14, 1980

[54] RECOVERY OF HYDROCARBON VAPORS FROM AIR

[75] Inventors: Keith D. Maguire; Royce A. Currieo, both of Sand Springs, Okla.

[73] Assignee: Youngstown Sheet and Tube Company, Youngstown, Ohio

[21] Appl. No.: 7,351

[22] Filed: Jan. 29, 1979

[51] Int. Cl.³ .................. B01D 47/00; C07C 7/05; B01D 3/10
[52] U.S. Cl. .......................... 55/85; 55/89; 203/9; 203/77; 585/806; 585/807
[58] Field of Search .......... 585/806, 807; 55/84, 55/85, 89, 93; 203/9, 77

[56] References Cited

U.S. PATENT DOCUMENTS

| 2,575,341 | 11/1951 | Gollmar | 55/85 |
| 2,804,939 | 9/1957 | Mattix | 55/85 |
| 2,816,943 | 12/1957 | DeLaplaine | 203/77 |
| 2,904,606 | 9/1959 | Williams | 585/806 |
| 3,719,720 | 3/1973 | Bir et al. | 585/806 |

OTHER PUBLICATIONS

Chemical Abstracts, vol. 91, 1979, pp. 284-285, Article #43983.
Chemical Abstracts, vol. 88, 1978, p. 343, Article #196680.

Primary Examiner—Tim R. Miles
Assistant Examiner—Gregory N. Clements
Attorney, Agent, or Firm—Vinson & Elkins

[57] ABSTRACT

The recovery of a hydrocarbon capable of autopolymerization from an air stream by absorbing the hydrocarbon with a plasticizer and separating the hydrocarbon from the plasticizer by vacuum and atmospheric distillation.

6 Claims, 1 Drawing Figure

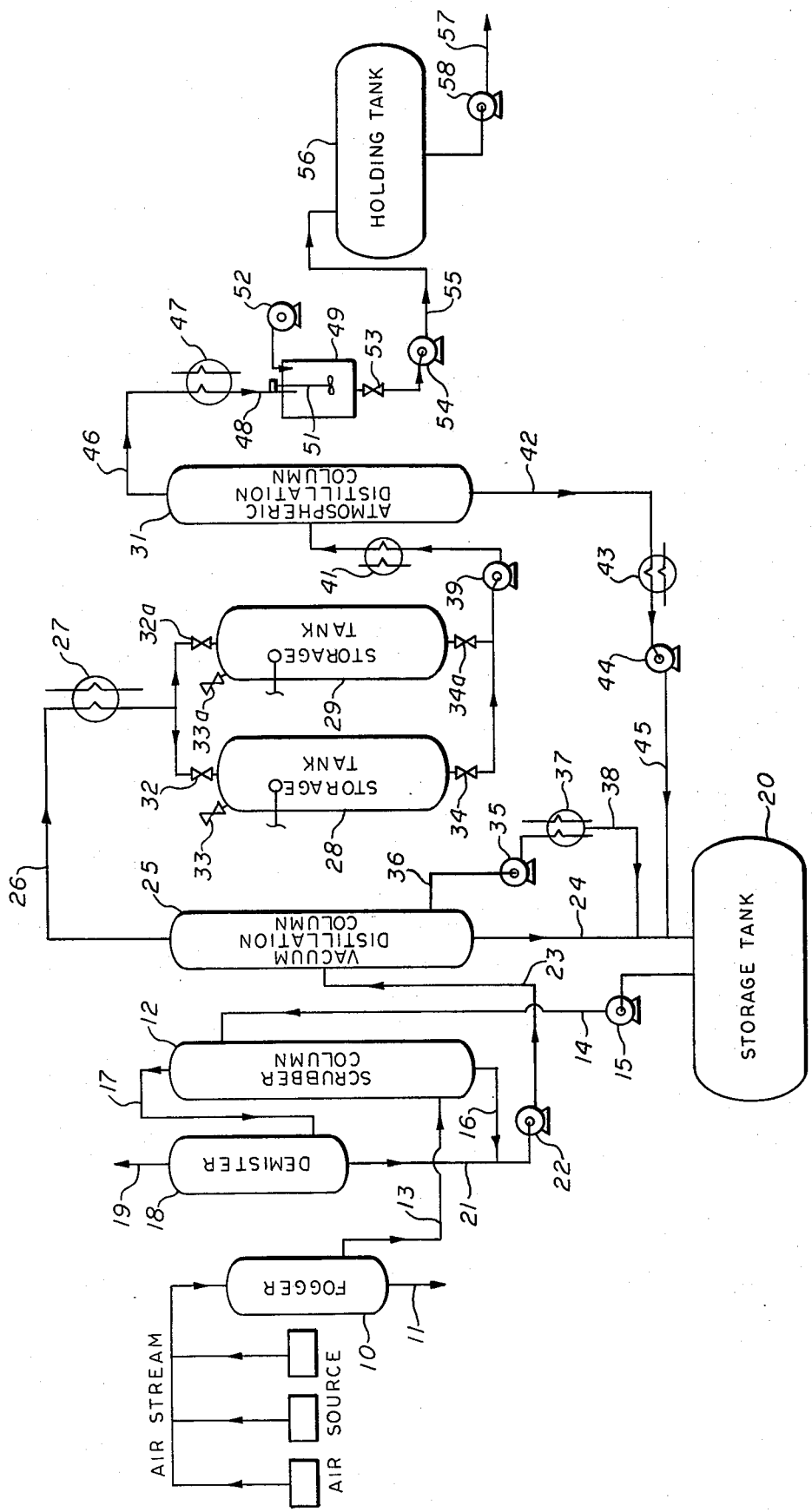

RECOVERY OF HYDROCARBON VAPORS FROM AIR

This invention relates to the recovery of hydrocarbon vapors from air and more particularly relates to the recovery of hydrocarbon vapors capable of auto-polymerization utilizing a high boiling point liquid plasticizer as an absorption medium.

Many manufacturing processes result in air within the building being contaminated with hydrocarbon vapors. In many plants in the past ventilation systems have been installed to exhaust the contaminated air to the outside, but this contributes to atmospheric pollution. In some instances the air contaminating vapors are valuable raw materials and should not be wasted if they can possibly be reclaimed economically. This invention is a closed loop system in which hydrocarbon can be removed from the air stream and processed to be reused at a later date.

It is common knowledge to pass an air stream contaminated with hydrocarbons through a filtering bed such as charcoal and adsorb the hydrocarbon in the bed. The bed can normally be regenerated with heat such as by passing steam through the bed. This system is not usable for certain hydrocarbons. For instance, one family of hydrocarbons has the characteristic of auto-polymerization and if they are absorbed in a bed, they are incapable of being recovered from the bed using ordinary procedures. For instance, styrene monomer will auto-polymerize and if collected in a bed some polymerization will occur during the collection step. The bed cannot be reactivated with steam or the like as the heat will cause auto-polymerization of the styrene in the bed and the bed will be ruined.

It is an object of this invention to provide a process of recovering hydrocarbon vapors capable of auto-polymerization.

It is another object of this invention to recover hydrocarbon vapors capable of auto-polymerization utilizing absorption and distillation techniques in which the absorbing medium is a plasticizer.

Another object is to provide a process of recovering hydrocarbons capable of auto-polymerization from air utilizing a liquid absorber in which the absorbing medium has substantially zero vapor pressure under conditions of contacting the absorber with an air stream and in which the absorbing medium and the absorbed hydrocarbon can be economically separated by distillation techniques, and in which the absorbing medium does not contaminate the recovered hydrocarbons so that they may be reused at a later date.

It is a specific object of this invention to remove waste styrene vapors from an air stream utilizing as an absorbing liquid a high boiling point liquid plasticizer which will not vaporize to any significant extent during the absorption step, which will not contaminate the styrene so that it may be reused at a later date, and which can be economically separated from the recovered styrene so that both the absorber and the recovered styrene are available for reuse.

Another object is to provide a process of recovering an aromatic or aliphatic hydrocarbon capable of auto-polymerization such as styrene monomers from air utilizing a high boiling point liquid plasticizer as an absorbing medium, which plasticizer does not contaminate the hydrocarbon and separating the plasticizer and absorbed hydrocarbon by a vacuum distillation step in which a rough separation is made and an atmospheric distillation step under elevated temperature in which a final separation of the hydrocarbon and plasticizer is carried out.

Other objects, features and advantages of this invention will be apparent from the drawing, the specification and the claims.

The drawing is a single FIGURE schematically illustrating the preferred system for carrying out the process of this invention.

The invention is the recovery of aromatic or aliphatic hydrocarbon vapors from an air stream which vapors are capable of auto-polymerization and hence are difficult to recover while maintaining them in the monomer form. A prime example of such a hydrocarbon is styrene monomer vapors which are a contaminant in plants manufacturing plastic pipe. The styrene monomer vapors cannot be recovered in adsorption beds as they will polymerize and the beds cannot be regenerated. In accordance with this invention a family of absorbers has been discovered which can be utilized to scrub the styrene vapors from the air stream. This family of absorbers are plasticizers which have substantially zero vapor pressure at the temperature of the scrubbing step so that the plasticizer does not contribute significantly to contamination of the air stream. These plasticizers are referred to as high boiling point plasticizers and will normally have a boiling point above about 300° C. at 760 MM Hg. The optimum compounds are those which combine the low vapor pressure with low freezing point and low viscosity making them readily pumpable to optimize the absorption recovery process. They should also be characterized by not contaminating the recovered hydrocarbon so that it may be reused at a later date. The family of high boiling point liquid pthalates including dibutyl phthalate, diisobutyl phthalate, diisodecyl phthalate, butyl benzyl phthalate, di iso octyl phthalate, together with alkyl aryl phosphate, n-butyl palmitate, glycols and their derivatives, are preferred. These compounds have a high boiling point of over about 300° C. at 760 MM Hg. They have low vapor pressure, low freezing point, and low viscosity. They will not contaminate styrene and can be readily separated from styrene monomer.

Particularly in regard to styrene monomer, these plasticizers are characterized by (1) very low, essentially zero vapor pressure at the temperature of the scrubbing operation, (2) they are mixable with styrene in all proportions, (3) they are stable, inert, noncorrosive, odorless, and nontoxic, (4) they have low viscosity, (5) they are inexpensive, and (6) they do not contaminate the recovered styrene so that it may be reused at a later date. Preferably dibutyl phthalate (DBP) has been found to be an excellent medium for absorbing styrene. Data has been accumulated on trace concentration levels of styrene in air. The data indicates that the operating efficiency of the system is inversely proportional to the temperature. Assuming that ideal solutions and gasses are employed the relationship is predicted by Raoult's Law, and thus a relatively low temperature is preferably maintained during the scrubbing step. For example, it is preferred that both the air stream being scrubbed and the plasticizer, such as DBP, used in the scrubbing step be cooled to about 70° F. before entering the scrubbing column.

As relatively high volumes of plasticizer are needed to scrub a high percentage of the hydrocarbon contaminant from the air stream, the plasticizer cannot economically be regenerated with high temperature distillation methods. Not only would an excessive amount of energy be necessary, but the capital investment for heat transfer equipment would be very substantial.

In accordance with this invention the plasticizer is regenerated by first subjecting the plasticizer and absorbed hydrocarbon to vacuum distillation to make a rough separation of the absorbed hydrocarbon and a small amount of the plasticizer from the remainder of the plasticizer. After this rough separtion is carried out the hydrocarbon may be separated from the plasticizer which came over as a distillate with the hydrocarbon by heating the distillate and separating it under atmospheric conditions. The auto-polymerization characteristic of a hydrocarbon such as styrene requires a substantial time frame for the polymerization to occur and it has been found that the styrene may be heated to substantially its boiling point and subjected to atmospheric distillation without an adverse percentage of auto-polymerization. Of course, immediately after the final separation the styrene monomer may have mixed therein the conventional inhibitors to inhibit polymerization.

While the invention relates to the recovery of hydrocarbons which are capable of auto-polymerization, it will be understood that virtually any other aromatic or aliphatic hydrocarbon which may exist in the air stream will also be absorbed by the plasticizer. If such occurs the distillation procedure should provide for separation of the hydrocarbons, such as by fractional distillation. By way of example, the preferred plasticizers listed above will absorb benzene, toluene, xylene, gasoline, and virtually any other aromatic or aliphatic compound, and if such compounds are present in the air stream being scrubbed, they will be recovered and can be separated out during the plasticizer regeneration process.

Examples of the ability of DBP to absorb styrene are given below. This data was collected utilizing an absorption column three inches in diameter filled with a suitable packing and divided into two stages of three feet each. The design was such that one or both of these stages could be used as desired.

EXAMPLE ONE

One stage of the column was used. Styrene concentration was measured continuously at the discharge end of the absorption column. DBP flow was measured to be 0.50 gallons per minute. The DBP was drawn from a holding tank and the DBP discharged from the scrubber column was returned to the same storage tank. The stream being scrubbed was 94.5 ppm styrene monomer.

(a) 12:45—Pump on, DBP flowing down the absorption column. DBP temperature 78° F.
(b) 12:50—Exhaust gas measured 14 ppm styrene, DBP temperature 78° F.
(c) 1:00—Exhaust gas measured 12 ppm styrene, DBP temperature 78° F.
(d) 1:15—Exhaust gas measured 27 ppm styrene, DBP temperature 82° F.
(e) 1:30—Exhaust gas measured 41 ppm styrene, DBP temperature 90°.
(f) 1:45—Pump off, DBP flow stopped, no absorption occurring in the column, exhaust gas measured 94.5 ppm styrene.

EXAMPLE TWO

In this example the gas stream contained 660 ppm styrene as determined by gas chromatography. The DBP flow through the column was 1.5 gallons per minute. The gas flow was 64 cubic feet per minute. Again, DBP was circulated from a single storage tank and returned to the storage tank. Only a single three foot stage of the scrubber column was used.

(a) 10:59—Pump on, DBP flowing through the column, flow rate of DBP measured 1.5 gallons per minute, DBP temperature 76° F. One column stage used.
(b) 11:05—Exhaust gas measured 215 ppm styrene, DBP temperature 82° F.
(c) 11:15—Exhaust gas measured 265 ppm styrene, DBP temperature 87° F.
(d) 11:18—Pump off, DBP flow through the column shut off, exhaust gas measured 660 ppm styrene.

EXAMPLE THREE

In this example the scrubber column was first utilized with single stage operation and then circulation was passed through two stages. The gas stream to the column contained 222 ppm styrene and the flow rate was 55–57 cubic feet per minute. The DBP temperature was maintained constant at 74° F. by heat exchanger and the flow rate of DBP was 1.3 gallons per minute. The DBP was withdrawn from and returned to the same storage tank.

| Time | | PPM Styrene in the Exhaust Gas |
|---|---|---|
| 2:10 | | 222 |
| 2:17 | Circulation thru one stage begins | |
| 2:25 | | 71 |
| 2:30 | | 69 |
| 2:35 | | 78 |
| 2:40 | Circulation thru two stages begins | |
| 2:45 | | 51 |
| 2:50 | | 51 |
| 2:55 | | 56 |
| 3:00 | | 56 |
| 3:05 | | 56 |
| 3:10 | Pump off - circulation stopped | |
| 3:15 | | 222 |

Examples of specific separations of styrene monomer and DBP are given below.

EXAMPLE FOUR

A preparation of 1000 grams DBP and 100 grams styrene monomer was separated by atmospheric distillation and 96.2 grams of the styrene monomer were recovered.

EXAMPLE FIVE

A feed of 0.03 mol percent styrene monomer in DBP was subjected to vacuum distillation at a pressure of 1 MM Hg and a temperature of 74° F. Vacuum distillation resulted in a 142 gram distillate. This distillate was distilled at atmospheric pressure at 278° F. temperature and a distillate of 127 grams of styrene monomer was obtained.

EXAMPLE SIX

A feed material of 0.026 mol percent styrene monomer in DBP was vacuum distilled under a pressure of 1.3 MM Hg. A distillate of 308 grams was obtained.

This distillate was distilled at atmospheric pressure and a distillate of 288 grams of styrene monomer obtained.

Reference is now made to the drawing which shows schematically the preferred method for carrying out this invention. The design is specifically directed at removing trace amounts of styrene monomer from a contaminated air stream such as would be found in a plastic pipe manufacturing facility, utilizing DBP as the absorbent.

The contaminated air stream is collected from several points in the plant and as the air temperature will normally be higher than desired the stream is introduced into the fogger 10. In the fogger 10 the stream is contacted with a spray of water to reduce the temperature of the air stream. The waste water is withdrawn via a conduit 11 and sent to the sanitary sewer. Preferably the fogger reduces the temperature of the contaminated air to about 70° F. This air is introduced into the bottom of the scrubber column 12 via conduit 13. The contaminated air rises in the scrubber column in counter-current flow with DBP which is obtained from the storage tank 20 and introduced into the scrubber column via conduit 14. Power for transferring the DBP is provided by pump 15. The scrubber column 12 is packed with suitable packing and the liquid DBP flows downwardly through the scrubber column in counter-current flow with the rising contaminated air stream. The DBP scrubs the styrene monomer from the rising air column. The DBP and absorbed styrene monomer leave the scrubber column through conduit 16. The clean air departs the top of scrubber 12 via conduit 17 and is passed through a demister 18. The demister 18 is again a packed vessel which acts to remove mist from the air stream before it is conveyed by line 19 to the atmosphere.

The liquid from the demister is conveyed via conduit 21 to the discharge line 16 from the scrubber column. This combined stream is pumped to the vacuum distillation column by pump 22. The absorber enters the distillation column via line 23 and is here distilled under vacuum conditions, preferably 5 MM Hg. A rough distillate is obtained which will be substantially all styrene monomer but will contain a small percentage of DBP. The remainder of the DBP which is essentially pure DBP exits through the bottom of the vacuum distillation column via line 24 to the storage tank 20.

The distillate from the vacuum distillation column 25 is conveyed via line 26 to the condensor 27 which liquifies the distillate.

Two storage tanks which operate alternately are provided at 28 and 29 for receiving the distillate from the condensor 27. While one of these tanks is receiving distillate, the other is discharging distillate to the atmospheric distillation column 31. Each tank is provided with shut-off valves 32 and 32a controlling flow of distillate into the tanks, with pressure relief valves 33 and 33a for controlling pressure on the storage tanks and draw-off valves 34 and 34a controlling flow of fluid to the atmospheric distillation column 31.

Liquid level controls automatically control the alternate operation of the two storage tanks. If it be presumed that storage tank 28 is filling, the atmospheric valve 33 and draw-off valve 34 are closed and the valve 32 open so that the tank 28 will receive distillate from the vacuum distillation column 25. At the same time the tank 29 will have its fill valve 32a closed, its vacuum relief valve 33a open so that the tank will be under atmospheric pressure and the draw-off valve 34a will be open so that storage tank 29 may discharge its contents into the atmospheric distillation column 31.

Providing the dual storage tank permits the ready accumulation of distillate from the vacuum distillation column under vacuum conditions until a suitable level of distillate is accumulated at which time the other tank is put on stream and the vacuum relieved and the contents of the tank directed to the atmospheric distillation column 31.

A suitable vacuum pump 35 is connected to the vacuum distillation column via line 36 and operates to maintain the desired vacuum in the vessel 25. The output from the vacuum pump may be directed through a trap 37 to recover any DBP vapors which might be drawn out by the vacuum pump. These vapors are liquified in the trap and transmitted to the storage tank 20 via line 38.

The DBP and absorbed styrene monomer are transferred from the storage tanks by pump 39 to the heat exchanger 41. In the heat exchanger 41 the temperature of the absorber is raised to approximately boiling point of styrene monomer and then introduced into the atmospheric distillation column 31. For example, the DBP and absorbed styrene monomer may be heated in exchanger 41 to a temperature of approximately 280° F. This is within a few degrees of the boiling point of styrene monomer and will insure substantially complete recovery of the styrene monomer as a distillate from the atmospheric distillation column 31 and a recovery of substantially pure DBP from the bottom of the column. The recovered DBP will be transferred from the column via line 42 to a heat exchanger 43 where it is cooled to a desired temperature, preferably 70° F. The cooled DBP is transmitted via pump 44 and line 45 to the storage tank for reuse.

The distillate from the atmospheric distillation column is transmitted via line 46 to the condensor 47 which cools the vapors and converts them to liquid form. The liquid styrene monomer is transmitted by line 48 to a mixing tank 49 where it is accumulated. When the desired amount of liquid styrene monomer is accumulated in the mixing tank 49, the mixer 51 is placed in operation and a suitable inhibitor is injected by the inhibitor metering pump 52 and mixed into the styrene monomer by the mixer 51. The inhibitor prevents the polymerization of the styrene monomer. After suitable mixing the draw-down valve 53 is opened and the contents of the tank 49 transmitted by pump 54 and line 55 to the holding tank 56 where it is kept until needed. The styrene monomer may then be transmitted via line 57 and pump 58 to process for reuse.

The foregoing disclosure and description of the invention is illustrative and explanatory thereof and various changes in the process may be made within the scope of the appended claims without department from the spirit of the invention.

We claim:
1. The process of recovering aliphatic or aromatic hydrocarbon vapors capable of auto-polymerization from air comprising,
   scrubbing an air stream containing said hydrocarbon vapors with a liquid plasticizer absorbent having substantially zero vapor pressure during the scrubbing step and which will not contaminate the hydrocarbon to absorb the hydrocarbon in the plasticizer, distilling the plasticizer and absorbed hydrocarbon under partial vacuum conditions to obtain a first distillate of plasticizer and the hydrocarbon, distilling the first distillate under atmospheric pressure to obtain a second distillate of the hydrocarbon, and separately recovering the hydrocarbon and the plasticizer.

2. The process of claim 1 wherein the hydrocarbon vapors are styrene monomer vapors.

3. The process of claims 1 or 2 wherein the plasticizer is selected from the group consisting of dibutyl phthalate, diisobutyl phthalate, diisodecyl phthalate, butyl benzyl phthalate, alkyl aryl phosphate, di iso octyl phthalate, n-butyl palmitate, and glycols and their derivatives.

4. The process of claims 1 or 2 wherein the plasticizer is a phthalate.

5. The process of claims 1 or 2 wherein the plasticizer is dibutyl phthalate.

6. The process of claims 1 or 2 wherein the partial vacuum is about 5 MM Hg absolute pressure, and the atmospheric pressure distillation is carried out at about the boiling point of the hydrocarbon being recovered.

* * * * *